(12) United States Patent
Vardiel et al.

(10) Patent No.: US 10,494,273 B2
(45) Date of Patent: Dec. 3, 2019

(54) METHOD AND APPARATUS FOR LIQUID DISINFECTION USING LIGHT TRANSPARENT CONDUIT

(71) Applicant: Atlantium Technologies Ltd, Beit-Shemesh (IL)

(72) Inventors: Zohar Vardiel, Or Yehuda (IL); Uri Levy, Rehovot (IL); Ytzhak Rozenberg, Ramat Gan (IL)

(73) Assignee: Atlantium Technologies Ltd, Beit-Shemesh (IL)

( * ) Notice: Subject to any disclaimer, the term of this patent is extended or adjusted under 35 U.S.C. 154(b) by 0 days.

(21) Appl. No.: 16/132,434

(22) Filed: Sep. 16, 2018

(65) Prior Publication Data

US 2019/0031536 A1    Jan. 31, 2019

Related U.S. Application Data

(63) Continuation of application No. 15/137,191, filed on Apr. 25, 2016, now Pat. No. 10,427,954, which is a
(Continued)

(51) Int. Cl.
*C02F 1/32* (2006.01)
*A61L 2/10* (2006.01)

(52) U.S. Cl.
CPC .............. *C02F 1/325* (2013.01); *A61L 2/10* (2013.01); *C02F 2201/007* (2013.01);
(Continued)

(58) Field of Classification Search
CPC .............. C02F 1/325; C02F 2201/3227; C02F 2201/3225; C02F 1/32
See application file for complete search history.

(56) References Cited

U.S. PATENT DOCUMENTS

| 1,940,580 A | 12/1933 | Caddy et al. |
| 2,776,565 A | 1/1957 | Hudon |

(Continued)

FOREIGN PATENT DOCUMENTS

| CN | 2587850 Y | 11/2003 |
| DE | 2622637 | 11/1977 |

(Continued)

OTHER PUBLICATIONS

Office Action for corresponding U.S. Appl. No. 11/917,878 dated Mar. 10, 2011.
(Continued)

*Primary Examiner* — Brooke Purinton
(74) *Attorney, Agent, or Firm* — Pearl Cohen Zedek Latzer Baratz LLP

(57) ABSTRACT

Some demonstrative embodiments of the invention include an illumination-based liquid disinfection device. The disinfection device may include, for example, a light transparent conduit to carry a flowing liquid to be disinfected, the conduit having an inlet to receive the liquid and an outlet to discharge the liquid, a substantially light transparent sleeve having external dimensions smaller than the internal dimensions of the conduit, the sleeve positioned within the conduit substantially perpendicular to the axis of symmetry of the conduit and a light source positioned within the sleeve.

4 Claims, 14 Drawing Sheets

Related U.S. Application Data continuation of application No. 13/892,328, filed on May 13, 2013, now Pat. No. 9,320,818, which is a continuation of application No. 11/917,878, filed as application No. PCT/IL2007/001409 on Nov. 14, 2007, now abandoned.

(60) Provisional application No. 60/858,727, filed on Nov. 14, 2006.

(52) U.S. Cl.
CPC ............. *C02F 2201/3225* (2013.01); *C02F 2201/3227* (2013.01); *C02F 2201/3228* (2013.01)

(56) References Cited

U.S. PATENT DOCUMENTS

| | | | |
|---|---|---|---|
| 3,637,342 A | | 1/1972 | Velos |
| 3,672,823 A | | 6/1972 | Boucher |
| 3,894,236 A | | 7/1975 | Hazelrigg |
| 4,149,228 A | | 4/1979 | Adamson |
| 4,237,008 A | | 12/1980 | Ratigan et al. |
| 4,367,410 A | | 1/1983 | Wood |
| 4,473,866 A | | 9/1984 | Davis |
| 5,124,131 A | | 6/1992 | Wekhof |
| 5,227,637 A | | 7/1993 | Heroid et al. |
| 5,261,874 A | | 11/1993 | Castle |
| 5,355,555 A | | 10/1994 | Zarelius |
| 5,503,800 A | * | 4/1996 | Free ................. C02F 1/325 250/432 R |
| 5,682,400 A | | 10/1997 | Kraznov |
| 5,785,845 A | | 7/1998 | Colalano |
| 5,994,705 A | | 11/1999 | Cooke et al. |
| 6,083,387 A | | 7/2000 | LeBlanc |
| 6,193,894 B1 | | 2/2001 | Hollander |
| 6,228,327 B1 | * | 5/2001 | Matschke ............. A61L 9/20 250/436 |
| 6,403,030 B1 | | 6/2002 | Horton, III |
| 6,761,270 B2 | | 7/2004 | Carew |
| 6,773,608 B1 | | 8/2004 | Hallett et al. |
| 6,871,534 B1 | | 3/2005 | Hamada et al. |
| 6,940,075 B2 | | 9/2005 | Shultz |
| 7,160,453 B1 | | 1/2007 | Matsumura et al. |
| 7,303,612 B2 | | 12/2007 | Morrow et al. |
| 7,329,029 B2 | | 2/2008 | Chaves et al. |
| 9,320,818 B2 | | 4/2016 | Vardiel |
| 10,137,213 B2 | * | 11/2018 | St. Louis ............. A61L 2/087 |
| 2003/0010927 A1 | | 1/2003 | Wedekamp |
| 2003/0019764 A1 | | 1/2003 | Baldwin et al. |
| 2003/0020785 A1 | | 1/2003 | Andrews |
| 2003/0049809 A1 | * | 3/2003 | Kaiser ................. A23L 3/28 435/173.1 |
| 2003/0129054 A1 | | 7/2003 | Manning et al. |
| 2003/0129105 A1 | | 7/2003 | Boehme |
| 2004/0004044 A1 | | 1/2004 | Anderson |
| 2004/0020862 A1 | | 2/2004 | Baca et al. |
| 2004/0109756 A1 | | 6/2004 | Wakazono et al. |
| 2004/0118786 A1 | | 6/2004 | Fraser et al. |
| 2004/0222163 A1 | * | 11/2004 | Saccomanno ............ A61L 2/10 210/748.11 |
| 2005/0003737 A1 | | 1/2005 | Montierth et al. |
| 2005/0173351 A1 | | 8/2005 | Neofotistos |
| 2006/0072318 A1 | | 4/2006 | Witham et al. |
| 2007/0012883 A1 | | 1/2007 | Lam |
| 2007/0114442 A1 | | 5/2007 | Chen et al. |
| 2007/0163934 A1 | | 7/2007 | Kim et al. |
| 2007/0207707 A1 | | 9/2007 | Montierth et al. |
| 2007/0274879 A1 | | 11/2007 | Millikin |
| 2007/0284315 A1 | | 12/2007 | Collins et al. |

FOREIGN PATENT DOCUMENTS

| | | |
|---|---|---|
| DE | 3828026 | 2/1990 |
| DE | 19714810 | 10/1998 |
| DE | 101 01 816 | 7/2002 |
| GB | 1584385 | 2/1981 |
| JP | 60-63050 | 4/1985 |
| JP | H04-55353 | 5/1992 |
| JP | 11216466 | 8/1999 |
| JP | 2002336896 | 11/2002 |
| WO | WO 03/033413 | 4/2003 |
| WO | WO 2004/033375 | 4/2004 |
| WO | WO 2005/011753 | 2/2005 |
| WO | WO 2008/059503 | 5/2008 |

OTHER PUBLICATIONS

Office Action for corresponding U.S. Appl. No. 11/917,878 dated Aug. 24, 2011.
Office Action for corresponding U.S. Appl. No. 11/917,878 dated Mar. 27, 2012.
Office Action for corresponding U.S. Appl. No. 11/917,878 dated Nov. 13, 2012.
Office Action for corresponding U.S. Appl. No. 12/470,277 dated Mar. 10, 2011.
Office Action for corresponding U.S. Appl. No. 12/470,277 dated Oct. 24, 2011.
Office Action for corresponding U.S. Appl. No. 12/470,277 dated Jun. 8, 2012.
Office Action for corresponding U.S. Appl. No. 12/470,277 dated Dec. 21, 2012.
Office Action for corresponding U.S. Appl. No. 12/774,489 dated Mar. 8, 2012.
Office Action for corresponding U.S. Appl. No. 13/892,328 dated Mar. 27, 2014.
Office Action for corresponding U.S. Appl. No. 15/137,191 dated Jun. 15, 2016.
Office Action for corresponding U.S. Appl. No. 15/137,191 dated Jan. 19, 2017.
Office Action for corresponding U.S. Appl. No. 15/137,191 dated Jul. 13, 2018.
Office Action for corresponding U.S. Appl. No. 15/137,191 dated Nov. 28, 2018.

* cited by examiner

METHOD AND APPARATUS FOR LIQUID DISINFECTION USING LIGHT TRANSPARENT CONDUIT

CROSS REFERENCE TO RELATED APPLICATIONS

This application is a continuation of U.S. application Ser. No. 15/137,191, filed on Apr. 25, 2016, which is a continuation of U.S. application Ser. No. 13/892,328, filed on May 13, 2013, issued as U.S. Pat. No. 9,320,818, on Apr. 26, 2016. U.S. application Ser. No. 13/892,328 is a continuation of U.S. application Ser. No. 11/917,878, filed on Jun. 8, 2010, which is a National Phase of PCT Application No. PCT/IL2007/001409, International filing date Nov. 14, 2007, claiming the benefit of US provisional patent application 60/858,727, filed on Nov. 14, 2006, all of which are incorporated herein by reference in their entirety.

BACKGROUND OF THE INVENTION

Ultraviolet liquid disinfection systems using UV light source located within a metallic chamber through which the liquid flow have been long known. The walls of such a metallic chamber absorb most of the incident UV light and light rays emitted from the UV light source traverse through the water once and are essentially absorbed by the metal. Accordingly, such systems do not utilize the light source in an efficient manner. There is a need for a UV disinfection system that would be more efficient than existing systems.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1A:
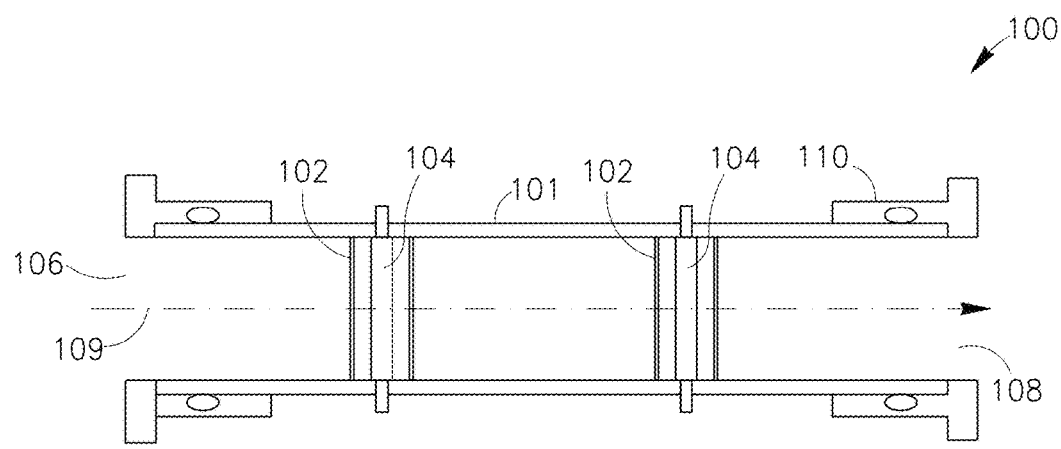
FIGS. 1A and 1B are conceptual illustrations of a disinfection system according to some demonstrative embodiments of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF EMBODIMENTS OF THE INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits may not have been described in detail so as not to obscure the present invention.

Some demonstrative embodiments of the invention include an ultraviolet (UV) disinfection system having a conduit to carry liquid to be disinfected and an illumination source located inside a transparent sleeve positioned substantially perpendicular to the longitudinal axis of symmetry of the conduit and the direction of flow of the liquid.

It will be appreciated that the liquid disinfection process may include inactivation or removal of any organism, bacteria, microorganism, being, creature, microbe, germ, virus, organic contaminator, non-organic contaminator, oxidizeable toxic or contaminator; any cumulative noxious species of biological or chemical origin; any oxidizing particle, fragment or element, e.g., Hydrogen peroxide or Titanium dioxide, intended to oxidize a contaminator and/or the like. Some demonstrative embodiments of the invention may refer to using ultraviolet (UV) light to disinfect the liquid and/or to oxidize particles within the liquid. However, it will be appreciated by those skilled in the art, that in other embodiments of the invention, light of any other suitable spectrum may be used.

Figure 1B:
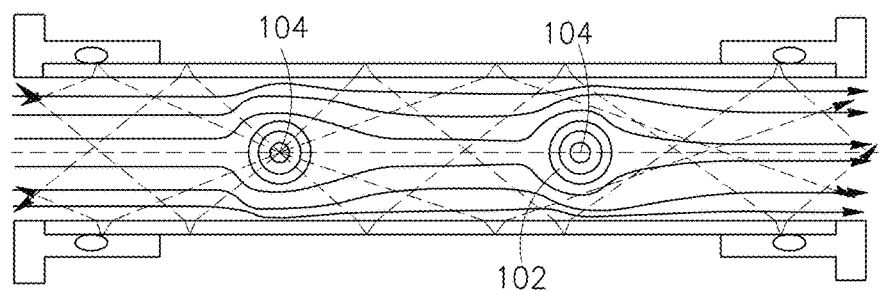

Reference is now made to FIGS. 1A and 1B, which conceptually illustrate a disinfection system according to some demonstrative embodiments of the invention. A disinfection system 100 may include a tube or conduit 101 to carry liquid to be disinfected, one or more substantially light-transparent sleeves 102 positioned within conduit 101 substantially perpendicular to its longitudinal axis of symmetry 109 and one or more light sources 104, each positioned within a respective sleeve 102. According to embodiments of the invention light sources 104 may be UV light sources capable of emitting light at 254 nm. Conduit 101 may have an inlet 106 to receive from an external liquid pipe the liquid to be disinfected and an outlet 108 to discharge the liquid via an external discharge pipe. System 100 may further include adaptors 110 to connect conduit 101 to the external liquid pipes. The adaptors may comprise O-rings to ensure water-tight connections between the external pipes and the conduit.

Conduit 101 may be substantially made of UV-transparent glass, such as quartz. UV-transparent sleeves 102 may be for example quartz or Teflon® sleeves. Each Sleeve 102 may have external dimensions smaller than the internal dimensions of conduit 101 such that liquid may flow within conduit 101 around sleeves 102. Both ends of sleeve 102 may extend from the walls of conduit 101 to enable replacement of light source 104 within sleeve 102. Light sources 104 may illuminate the liquid to be disinfected when flowing in the conduit. In this configuration, the liquid within conduit 101 may act as a waveguide and at least part of the light, for example, at least half of the emitted UV intensity, may be totally-internally reflected at the interface of the UV-transparent conduit 101 and the air surrounding it. Conduit 101 may be located inside a protective metal sleeve with an air gap between the conduit and the sleeve, as shown for example, in FIG. 2B. The total internal reflection (TIR) effect is demonstrated in FIG. 1B.

Although the invention is not limited in this respect, light source 104 may generate UV light of a suitable UV-germicidal spectrum. For example, light source 104 may include one or more UV lamps, e.g., a low-pressure UV lamp, a low-pressure high output UV lamp, a medium-pressure UV lamp, a high-pressure UV lamp, and/or a microwave-excited UV lamp, as are all known in the art.

According to embodiments of the invention, the liquid may act as a waveguide and at least part of the light, for example, at least half of the emitted UV intensity, may be totally-internally reflected at the interface of the glass conduit and air surrounding it. According to other embodiments of the invention, at least 70% of the emitted UV intensity may be totally-internally reflected at the interface of the glass conduit and air surrounding it. As shown, in FIG. 1B, the liquid to be disinfected may flow around each of light sources 104. In such a configuration, the system may include an additional light source to enable disinfection of the liquid to the required level even when one of the light sources 104 is fully or partially dysfunctional. For example, the disinfection process may continue while a non-functional light source is being replaced or fixed.

It should be noted that embodiments of the present invention, in which light sources 104 are located substantially perpendicular to the direction of flow of the liquid within conduit 101 may ensure that each light source is capable of illuminating substantially the entire flow of liquid when the flow traverses that particular light source.

Figure 2A:
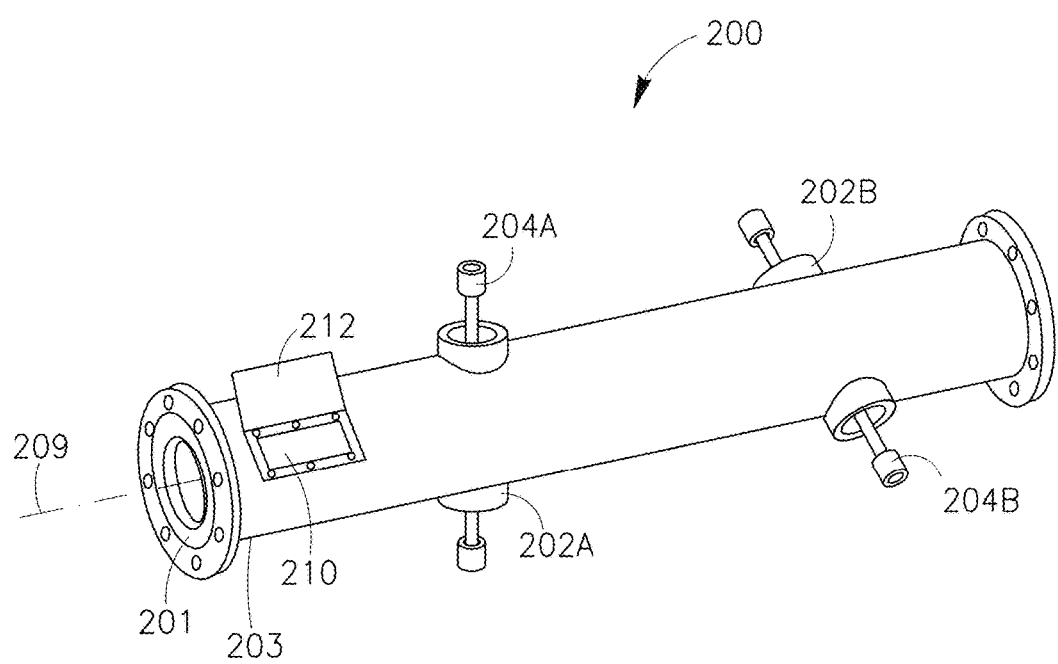
FIG. 2A is an illustration of an exemplary disinfection system according to some demonstrative embodiments of the invention.
Figure 2B:
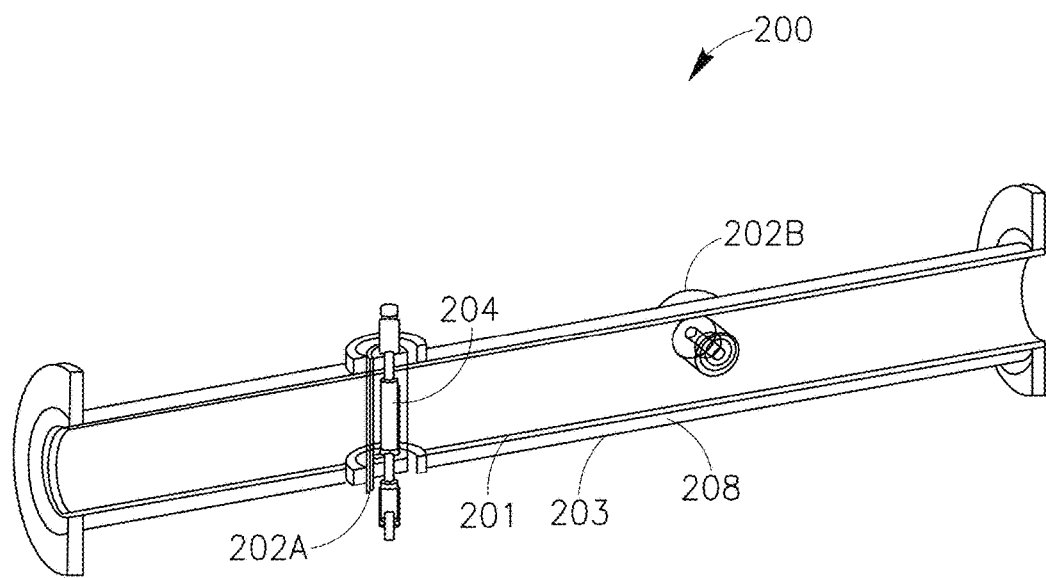
FIG. 2B is a cross sectional view of the exemplary disinfection system of FIG. 2A.

Reference is now made to FIG. 2A, which shows an exemplary disinfection system and to FIG. 2B, which is a cross sectional view of the exemplary disinfection system according to some embodiments of the invention. An exemplary disinfection system 200 may include a substantially UV-transparent conduit 201 to carry liquid to be disinfected, substantially UV-transparent sleeves 202A and 202B positioned within conduit 201 substantially perpendicular to its axis of symmetry 209 and one or more UV-light sources 204, each positioned within a respective sleeve 202. In this exemplary configuration, sleeves 202A and 202B are orthogonal to each other.

It should, however, be understood to a person skilled in the art, that according to embodiments of the present invention, UV-transparent sleeves 202 may be positioned with respect to each other, at any rotational angle around the longitudinal axis of symmetry 209 of conduit 201. According to other embodiments of the present invention, UV-transparent sleeves 202 may be positioned at any rotational angle around other axis of symmetry of conduit 201. Although a symmetrical cylinder-shaped conduit is shown, it should be understood to a man skilled in the art that the conduit may have other shapes, not necessarily symmetrical, as described in detail with respect to FIG. 5A-5C.

Conduit 201 may be located inside a protective metal tube 203 forming an air gap 208 between conduit 201 and metal tube 203. Although the scope of the present invention is not limited in this respect, external tube 103 may include a see-through window 210 made of transparent material such as glass, plastic or any other suitable material to enable an operator to view conduit 201 and a cover 212 to cover window 210 when desired. Although in the exemplary illustration of FIG. 2A, a single see-through window is shown, it should be understood to a person skilled in the art that the invention is not limited in this respect and according to embodiments of the present invention tube 203 may include more than one see-through window at any size and/or shape.

Figure 3:
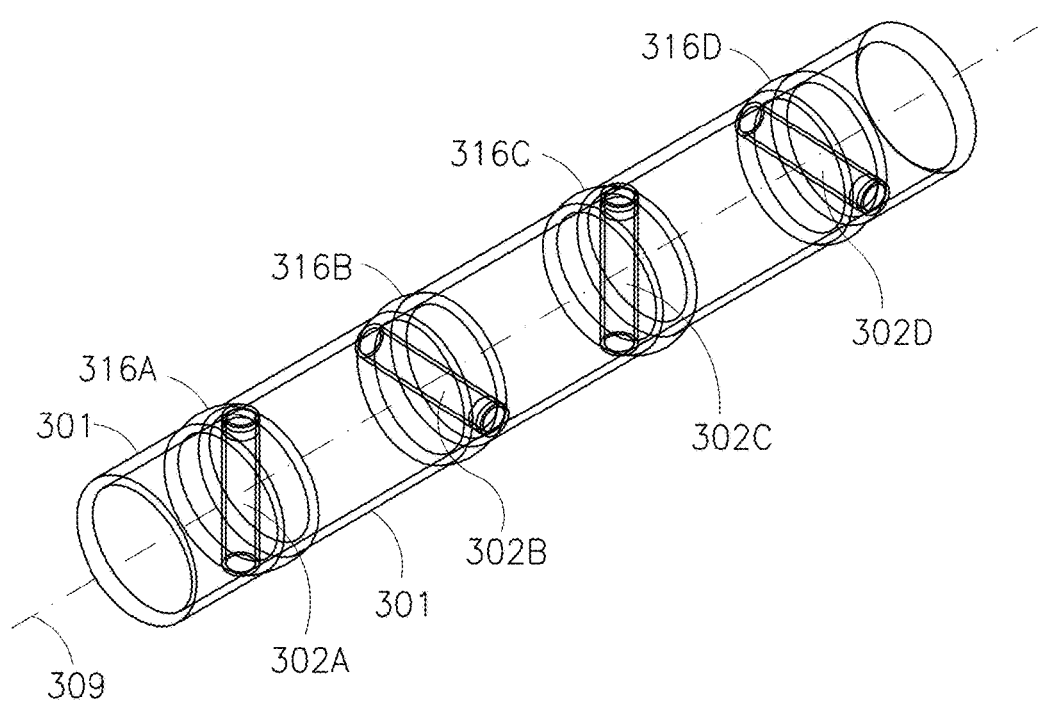
FIG. 3 depicts an exemplary illustration of a UV-transparent conduit according to some demonstrative embodiments of the invention.

Reference is now made to FIG. 3, which depicts an exemplary illustration of a conduit having four sleeves according to some demonstrative embodiments of the invention. The exemplary conduit 301 of FIG. 3 includes four UV-transparent sleeves 302A-302D positioned within conduit 301 substantially perpendicular to its longitudinal axis of symmetry 309. In this exemplary configuration, pairs of adjacent sleeves are orthogonal to each other. Accordingly, sleeves 302A and 302B are orthogonal to each other; sleeves 302B and 302C are orthogonal to each other; and sleeves 302C and 302D. Further, pairs of alternating sleeves are parallel to each other. Accordingly, sleeves 302A and 302C are parallel to each other; and likewise sleeves 302B and 302D are parallel to each other. It should, however, be understood to a person skilled in the art, that according to embodiments of the present invention, UV-transparent sleeves 302 may be positioned with respect to each other, at any rotational angle around the axis of symmetry 309 of conduit 301. Sleeves may be fused to conduit 301 to form a single glass structure.

According to other embodiments of the present invention, sleeve 202 may be attached to conduit 301 using housing, adaptors, connectors or any suitable means known in the art. For example, each of areas 316A-316D may be a metal housing for one of sleeves 302A-302D. The metal housing may be coated on its interior surface with a reflective coating to increase the efficiency of the disinfection process. According to embodiments of the invention, the reflective coating may be coated with a UV-transparent, UV resistive and bio-compatible coating, for example a Teflon® coating.

Although, the sleeves are illustrated as being cylindrical, it should, be understood to a person skilled in the art that embodiments of the invention are not limited in this respect and the sleeve may have other suitable shapes, such as hydrodynamic shapes, as detailed below with respect to FIG. 7.

Figure 4:
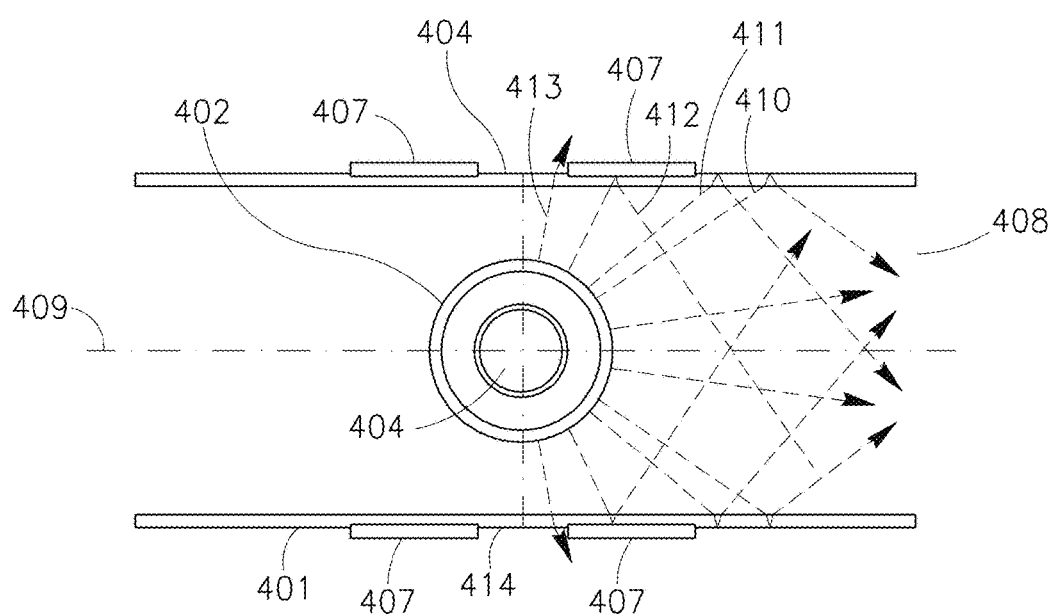
FIG. 4 is a side view of a conceptual illustration of an exemplary UV-transparent conduit having a reflective coating on portions of its surface according to some demonstrative embodiments of the invention.

Reference is now made to FIG. 4, which conceptually illustrates a side view of an exemplary conduit having a reflective coating on portions of its surface according to some embodiments of the invention. A sleeve 402 may be positioned within conduit 401 such that sleeve 402 is substantially perpendicular to the longitudinal axis of symmetry 409 of conduit 401. UV-light source 404 may be positioned within sleeve 402. As both sleeve 402 and conduit 401 are substantially transparent to UV light, the liquid may act as a waveguide and at least part of the light, for example, rays 410 and 411 may be totally-internally reflected at the interface of conduit 401 and the air surrounding it 408.

Still, rays such as ray 413 having an angle with the surface of the conduit above a critical angle cannot undergo total internal reflection (TIR). Such a ray is transmitted outside the liquid after traversing the liquid only once. Conduit 401 may include one or more mirrors or UV reflective coating areas 407 to reflect non-guided rays, for example, ray 412 back into the liquid.

According to some embodiments of the present invention, at least portions of the exterior surface of conduit 401 may be coated with UV reflective coating 407 to produce rear surface mirror effect, e.g., to allow a larger portion of the light from light source 404 to illuminate the liquid flowing in conduit 401. Coating 407 may reflect back into the liquid additional light rays reaching the surface in relative proximity to sleeve 402. Reflective coating 407 may comprise aluminum deposition, gold deposition or multi-layer dielectric material. Any other suitable reflective coating may be used. According to other embodiments of the invention, the entire surface of the conduit may be coated with reflective coating to enhance the back-mirror effect.

Although the scope of the present invention is not limited in this respect, at least a portion of conduit 401, e.g., area 414 surrounding light source 404 may be from a material having UV-reflection properties, for example, aluminum or any other metal. Reflecting area 414 may reflect back into the liquid non-guided light rays that cannot undergo TIR, such as ray 413. Reflecting area 414 may include a UV-reflecting coating on its inner surface or may be covered by a thin sheet made of material having UV-reflecting properties. The UV-reflecting coating or sheet may be protected against water damage by coating it with a UV-resistive, UV-transparent coating such as Teflon®.

Figure 5A:
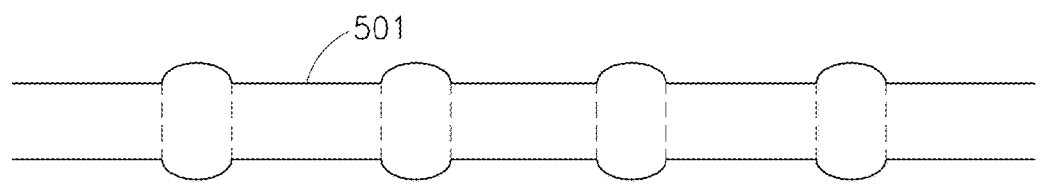
FIGS. 5A-5C are schematic illustrations of conduits according to some demonstrative embodiments of the invention.
Figure 5B:
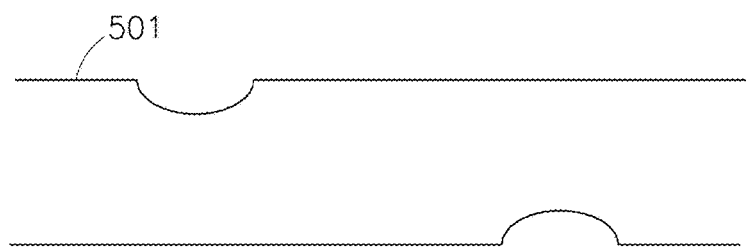
Figure 5C:
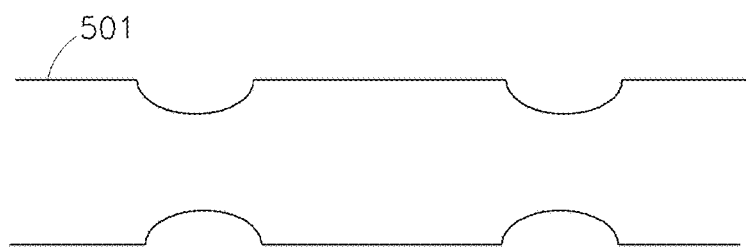

Reference is now made to FIGS. 5A, 5B and 5C, which depict schematic illustrations of conduits having varying diameters along their lengths according to some demonstrative embodiments of the invention. The shape of the conduit may be pre-determined to increase the efficiency of the disinfection process. According to embodiments of the present invention, the internal diameter of conduit 501 may vary along its length, as depicted in the demonstrative illustration of FIGS. 5A, 5B and 5C. The specific shape of the conduit may affect the liquid flow pattern and the shape may be pre-determined in order to increase the overall efficiency of the disinfection system. It should be understood that conduit 501 may have any other symmetrical or non-symmetrical shape.

Figure 6A:
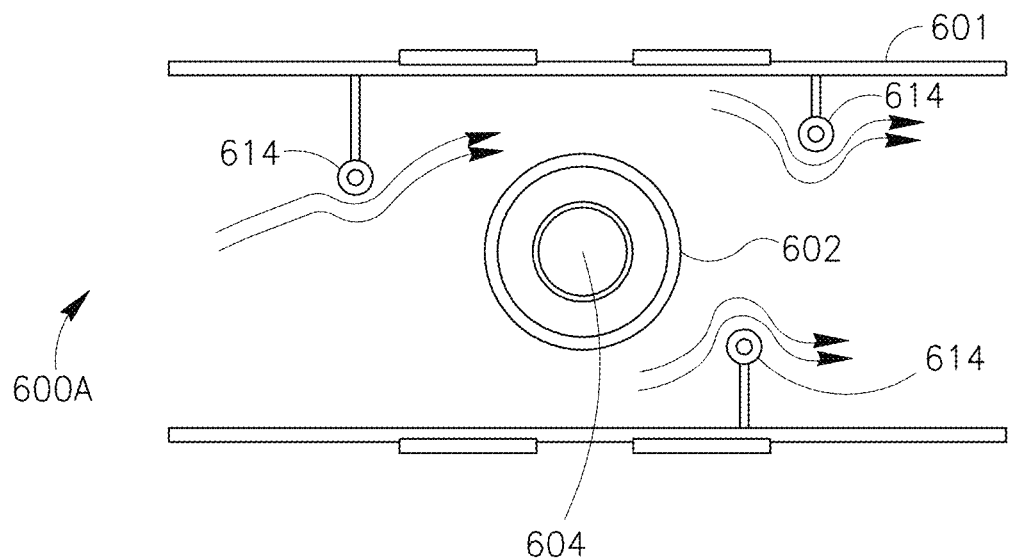
FIGS. 6A and 6B are illustrations of disinfectors having flow-forming objects according to some demonstrative embodiments of the invention.
Figure 6B:
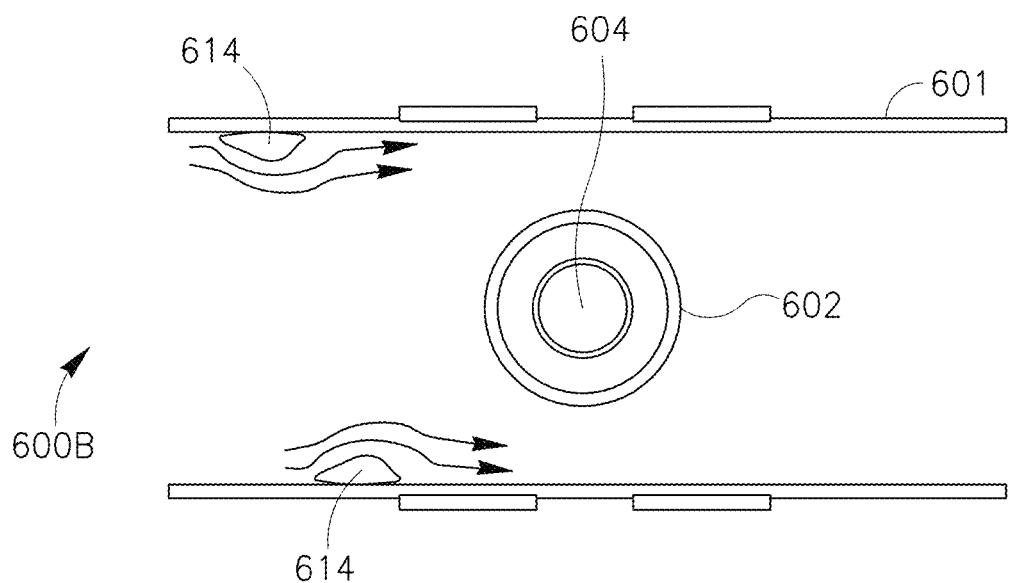

Reference is now made to FIGS. 6A and 6B, which depict schematic illustrations of a portion of disinfection systems having flow-forming objects according to some embodiments of the present invention. Each of disinfection systems 600A and 600B may include a conduit 601 to carry liquid to be disinfected, a substantially UV-transparent sleeves 602 positioned within conduit 601 substantially perpendicular to its longitudinal axis of symmetry and a UV-light sources 604 positioned within sleeve 602. Conduit 601 may include one or more objects 614 affixed to the conduit. As illustrated in FIG. 6A, objects 614 may be attached to a protrusion to be located in relative distance from the surface of the conduit. As illustrated in FIG. 6B, objects 614 may be attached to the surface of the conduit or located in relative proximity to the surface. Objects 614 may be pre-designed and may be located in specific positions in conduit 601 to affect the liquid flow pattern. Additionally or alternatively, UV-transparent objects and/or UV-scattering objects and/or UV-reflective objects may be affixed, attached or added to conduit 601. The flow-forming objects may affect the liquid flux and the distribution of liquid tracks and the objects shape and location may be pre-determined in order to increase the overall efficiency of the disinfection process. The light scattering objects and/or light reflective objects may influence the spatial distribution of UV light intensity and the objects shape and location may be pre-determined in order to increase the overall efficiency of the disinfection process.

Figure 7:
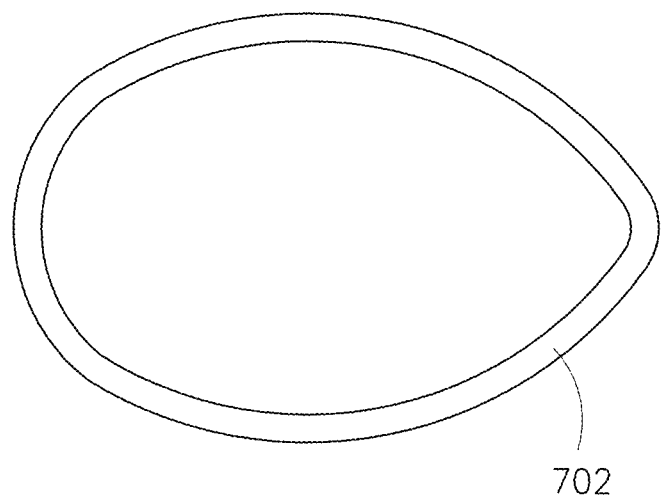
FIG. 7 is a cross section schematic illustration of a non-cylindrical sleeve according to some demonstrative embodiments of the invention.

Reference is now made to FIG. 7, which depict schematic cross section illustration of non-cylindrical sleeve according to some demonstrative embodiments of the invention. According to embodiments of the present invention, sleeve 702 may have a hydrodynamic shape to prevent the formation of liquid stagnation zone where liquid may flow at a low velocity in proximity to sleeve 702 at the area facing the outlet of the conduit. The specific shape of sleeve 702 may be designed to improve light distribution and liquid flow pattern in order to increase the overall efficiency of the disinfection system. It should be understood to a person skilled in the art that sleeve 702 having a non-cylindrical shape may be positioned within a substantially UV-transparent conduit substantially perpendicular to the direction of liquid flow. Alternatively, the non-cylindrical sleeve may be positioned within non-transparent containers such as stainless steel conduits or reactors.

Figure 8:
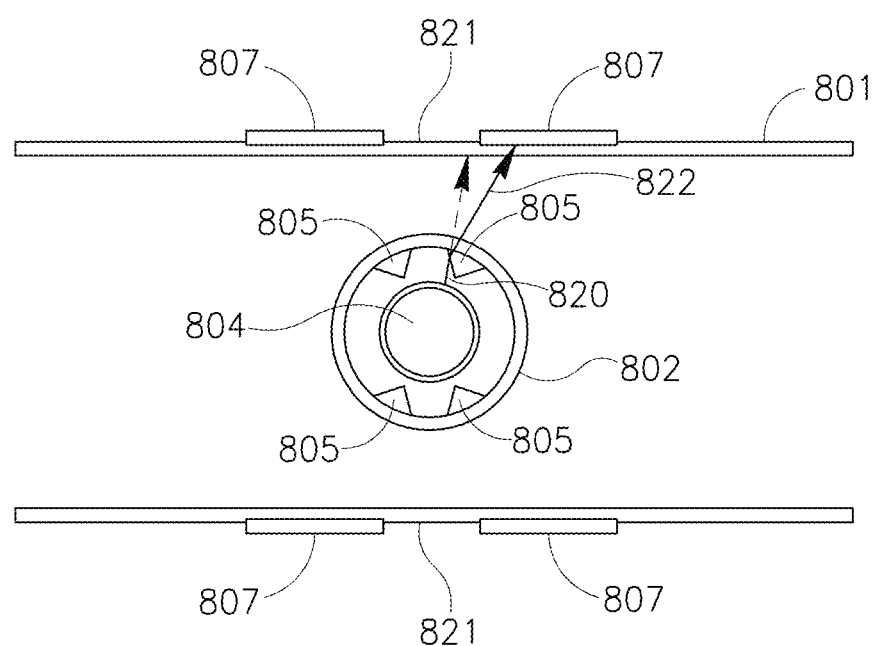
FIG. 8 is a conceptual illustration of an exemplary disinfection system having a patterned sleeve according to some demonstrative embodiments of the invention.

Reference is now made to FIG. 8, which is a conceptual illustration of an exemplary disinfection system having a patterned sleeve according to some demonstrative embodiments of the invention. A sleeve 802 may be positioned within conduit 801 such that sleeve 802 is substantially perpendicular to the longitudinal axis of symmetry of conduit 801. UV-light source 804 may be positioned within sleeve 802. As both sleeve 802 and conduit 801 are substantially transparent to UV light, the liquid may act as a waveguide and at least part of the light may be totally-internally reflected at the interface of conduit 801 and its surroundings. For another portion of the light that cannot undergo TIR, conduit 801 may include one or more mirrors or UV reflective coating areas 807 to reflect rays back into the liquid. Still, certain rays may evade both TIR and the UV reflective areas.

According to embodiments of the invention, sleeve 802 may include one or more objects 805 located in specific positions and shaped in order to influence the light distribution inside conduit 801. Object 805 may be UV-scattering or UV-reflecting objects made of any suitable material. For example, ray 820 is directed toward area 821, which is not coated with reflective coating. Accordingly, in a non-patterned sleeve such a ray would traverse the liquid for a short distance before exiting the conduit via area 821. Instead by using sleeve 802, ray 820 may hit object 805, change its direction (arrow 822) and reach reflective area 807 to be reflected back into the liquid.

Although, the patterned sleeve is described as being positioned within a substantially UV-transparent conduit substantially perpendicular to the direction of liquid flow, it should, be understood to a person skilled in the art that embodiments of the invention are not limited in this respect and embodiments of the invention are likewise applicable to using such a patterned sleeve at any position relative to the liquid flow within any container or conduit including non-transparent containers such as stainless steel conduits or reactors.

Figure 9:
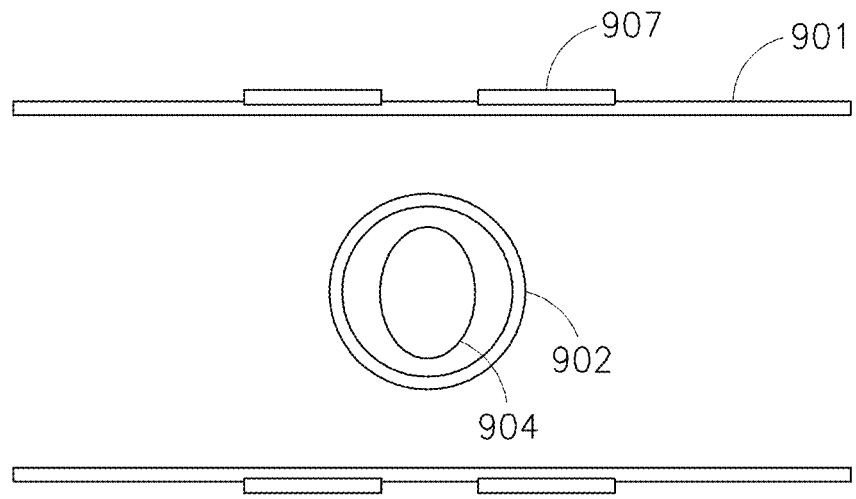
FIG. 9 is a conceptual illustration of an exemplary disinfection system having a non-cylindrical light source according to some demonstrative embodiments of the invention.

Reference is now made to FIG. 9, which is a conceptual illustration of an exemplary disinfection system having a non-cylindrical light source according to some demonstrative embodiments of the invention. A sleeve 902 may be positioned within conduit 901 such that sleeve 902 is substantially perpendicular to the longitudinal axis of symmetry of conduit 901. UV-light source 904 may be positioned within sleeve 902. As both sleeve 902 and conduit 901 are substantially transparent to UV light, the liquid may act as a waveguide and at least part of the light may be totally-internally reflected at the interface of conduit 901 and its surroundings. For another portion of the light that cannot undergo TIR, conduit 901 may include one or more mirrors or UV reflective coating areas 907 to reflect rays back into the liquid. Light source 904 may have a non-cylindrical geometry; for example, its cross section may be an ellipse or any other desired shape to generated controlled light distribution. For example, the shape of the lamp may be directed to generate a non-circular light distribution such that more light rays would be directed to the direction of the liquid flow than to the surface of conduit 901. The specific shape of light source 904 may be designed according to the specific characteristics of the system's geometry and the disinfection process in order to increase the overall efficiency of the disinfection system.

Although, the non-cylindrical light source is described as being positioned within a substantially UV-transparent conduit substantially perpendicular to the direction of liquid flow, it should, be understood to a person skilled in the art that embodiments of the invention are not limited in this respect and embodiments of the invention are likewise applicable to using such a light source at any position relative to the liquid flow within any container or conduit including non-transparent containers such as stainless steel conduits or reactors.

Figure 10:
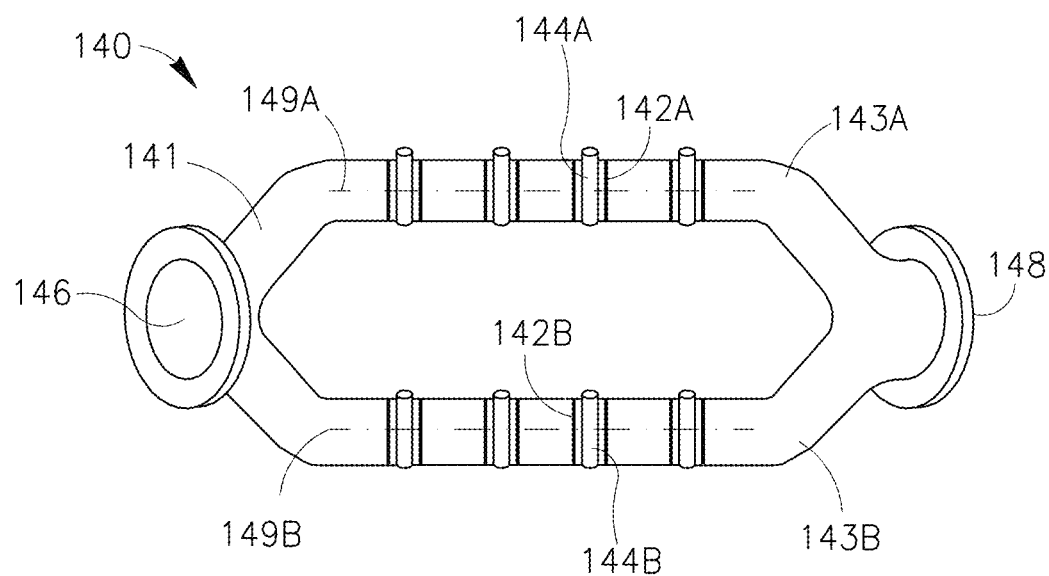
FIG. 10 is a schematic illustration of a 2-pipe disinfection system according to some demonstrative embodiments of the invention.

Reference is now made to FIG. 10, which depicts an exemplary illustration of a 2-pipe disinfection system according to embodiments of the invention. A disinfection system 140 may include a conduit 141 to carry liquid to be disinfected. Conduit 141 may include more than one branch, for example two branches, 143A and 143B to increase the liquid flow. Having more than one branch may enable better control of the internal pressure in conduit 141. Conduit 141 may have an inlet 146 to receive from an external liquid pipe the liquid to be disinfected and an outlet 148 to discharge the liquid via an external discharge pipe.

System 140 may include one or more substantially UV-transparent sleeves 142A positioned within branch 143A substantially perpendicular to its longitudinal axis of symmetry 149A and one or more UV-light sources 144A, each positioned within a respective sleeve 142A. System 140 may further include one or more substantially UV-transparent sleeves 142B positioned within branch 143B substantially perpendicular to its longitudinal axis of symmetry 149B and one or more UV-light sources 144B, each positioned within a respective sleeve 142B.

It should be understood to a person skilled in the art that although a 2-brance conduit is described, embodiments of the invention are not limited in this respect and a disinfection system according to other embodiments of the present invention may include more than 2 branches for liquid flow.

Figure 11A:
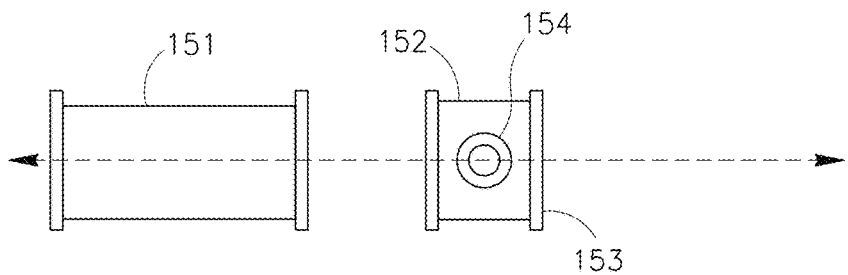
FIGS. 11A-11C are exemplary illustrations demonstrating the modular nature of a disinfection system according to embodiments of the invention.
Figure 11B:
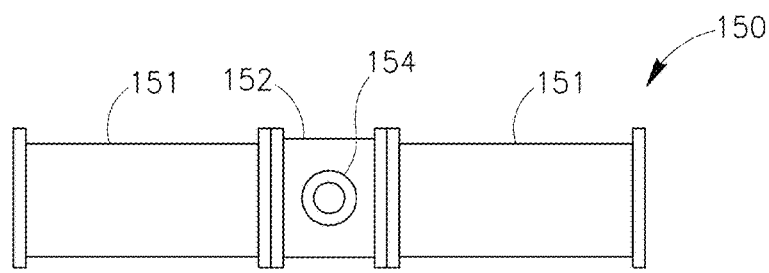
Figure 11C:
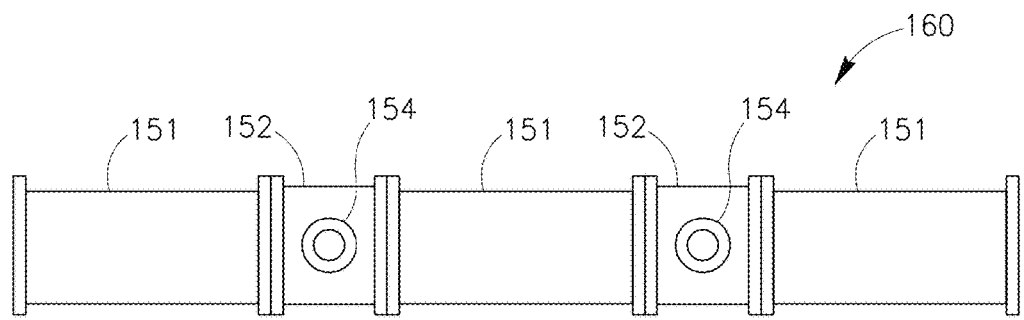

FIGS. 11A-11C demonstrate the modular nature of an exemplary disinfection system according to embodiments of the invention. According to some embodiments of the present invention, the liquid flow section of the disinfection system may be constructed from two types of modular building blocks, conduit elements 151 and sleeve elements 152. Sleeve elements 152 may include a ring 153 having a UV-transparent sleeve 154 positioned within. The internal diameter or ring 153 is larger than the external diameter of sleeve 154. Element 152 may further include a UV-light source positioned within sleeve 154. Both ends of element 152 may include adaptors, connectors or a screw mechanism to be connected to one or more of conduits 151. Conduit elements 151 may be substantially made of UV-transparent material, such as quartz as described in detail above. The external diameter of conduit 151 may be substantially similar to the external diameter of ring 153. Both ends of conduits 151 may include adaptors, connectors or a screw mechanism to be connected to one or more of elements 152. The connections between conduits 151 and sleeve parameters 152 may be water-tight connections.

Although the scope of the present invention is not limited in this respect, at least one sleeve element 152 and two conduit elements 151 may create a conduit set to carry liquid to be disinfected as described above. A conduit set may comprise a number of n sleeve elements 152 and a number of n+1 conduit elements 151. For example, as shown in FIG. 11B conduit 150 may comprise one sleeve element 152 and two conduit elements 151. Another example, shown in FIG. 11C, conduit 160 may comprise two sleeve elements 152 and three conduit elements 151.

Although in the exemplary illustration of FIGS. 11A-11C, conduits 150 and 160 are shown, it should be understood to a person skilled in the art that the invention is not limited in this respect and according to embodiments of the present invention any combination of n+1 conduit elements 151 and n sleeve elements 152 may be connected to create a conduit set.

Although, embodiments of the present invention are not limited in this respect, it is understood and simulated that a pre-designed structure according to embodiments of the present invention improves the efficiency of UV disinfection and increase kill probability, namely the probability to inactivate the entities being in the liquid flowing in conduit 101.

Computer Simulations

Following, are examples relating to illumination flux distributions in accordance with some demonstrative embodiments of the invention. It should be noted that the illumination-flux distributions used in these examples are not intended to limit the scope of the invention to any particular configuration and/or illumination flux distribution.

Figure 12A:
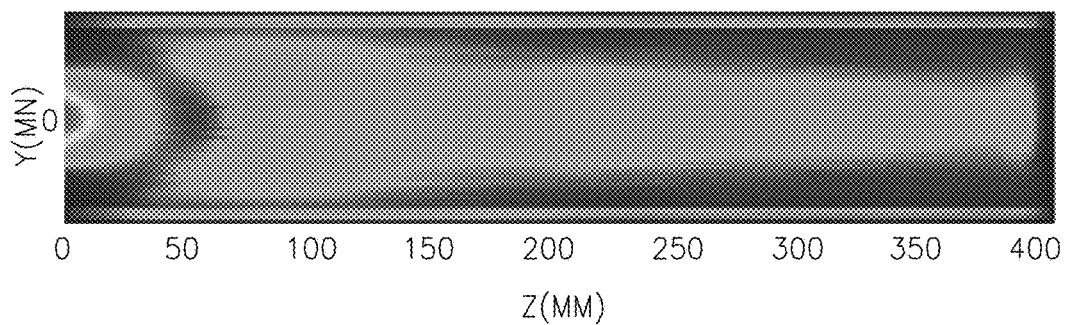
FIGS. 12A-12C are schematic illustrations of light flux distribution within an exemplary conduit based on computer simulations according to embodiments of the invention.
Figure 12B:
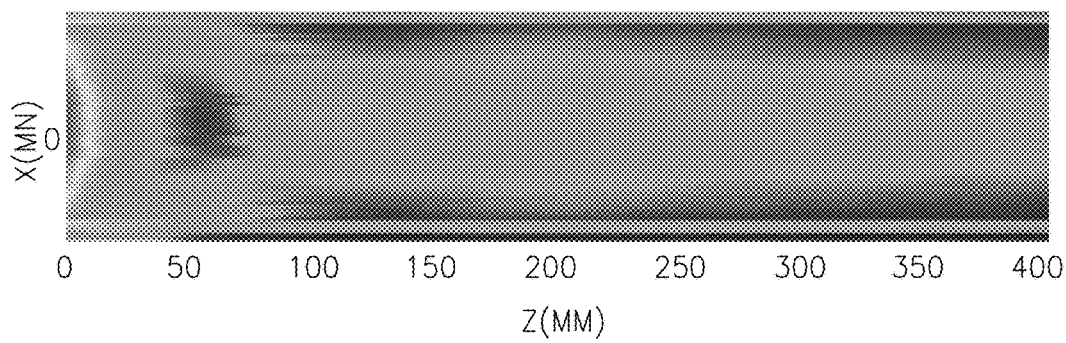
Figure 12C:
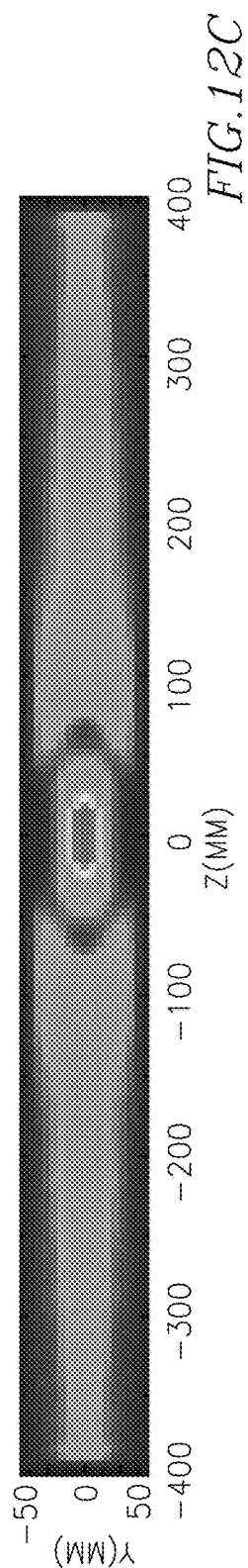

FIGS. 12A-12C illustrate computer simulations of light flux distribution within an exemplary conduit during a liquid disinfection process. The simulated system is an exemplary system according to embodiments of the invention. The system includes one UV light source within a quartz sleeve positioned in the center of a quartz conduit such that the sleeve is perpendicular to the longitudinal axis of symmetry of the conduit defining the Z direction. The longitudinal axis of the sleeve defined the X direction. The calculations were performed for a flow of liquid of 50 m$^3$/h. The length of the conduit was taken to be 800 mm, the internal diameter of the conduit as 75 mm, the external diameter of the sleeve protecting the UV light source as 44 mm and the pressure drop as ΔP (at 50 m$^3$/h)=0.27 [bar]. The liquid used for the computer simulations was clear water with UVT (ultraviolet transmission) of 98%.

Figure 12D:
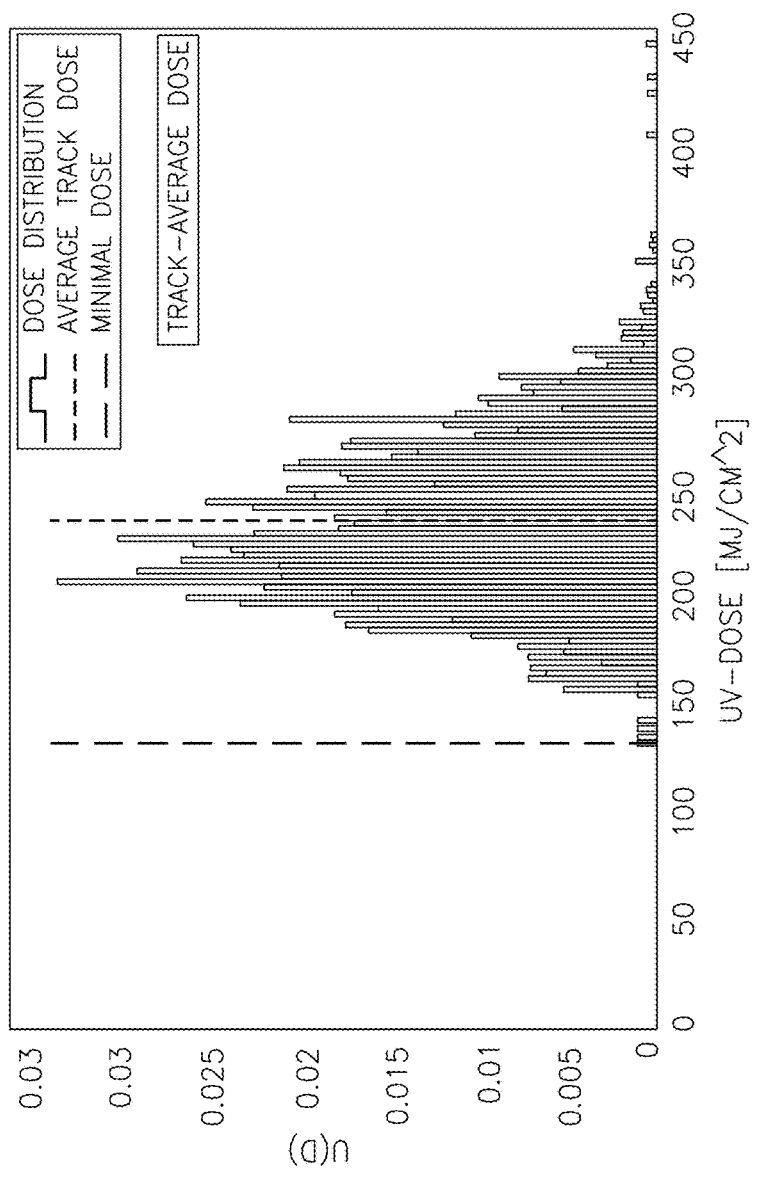
FIG. 12D is a dose distribution histogram associated with the simulation of FIGS. 12A-12C.

FIG. 12A is a cross section in the Y-Z plane of a portion of the conduit illustrating the light flux distribution between the light source and the outlet end of the conduit. FIG. 12B is a cross section in the X-Z plane of the same portion of the conduit illustrating the light flux distribution between the light source and the outlet end of the conduit. FIG. 12C is a cross section in the Y-Z plane of the entire conduit illustrating the light flux distribution between the inlet end and the outlet end of the conduit. As can be seen, the light reaches trough the entire length of the tube at a substantial intensity. FIG. 12D shows a graph illustrating the calculated normalized UV dose distribution within the quartz conduit. The normalized dose distribution function is closed to being a Gaussian function.

Figure 13A:
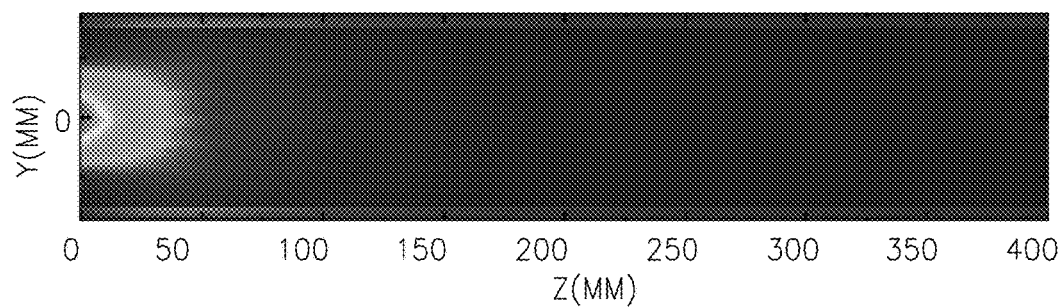
FIGS. 13A-13B are schematic illustrations of light flux distribution within a stainless steel conduit based on computer simulations according to embodiments of the invention.
Figure 13B:
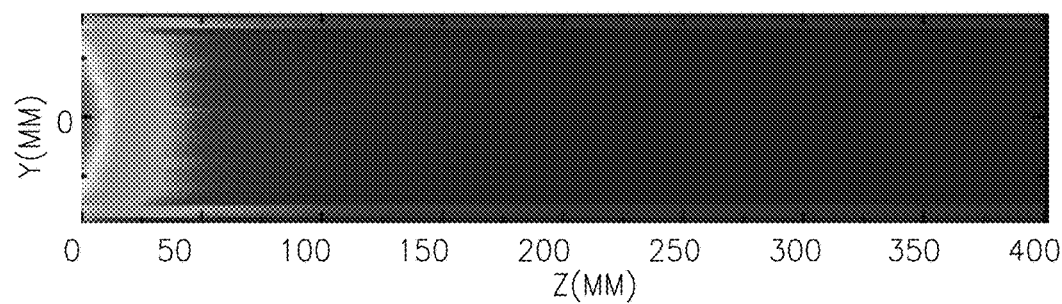
Figure 13C:
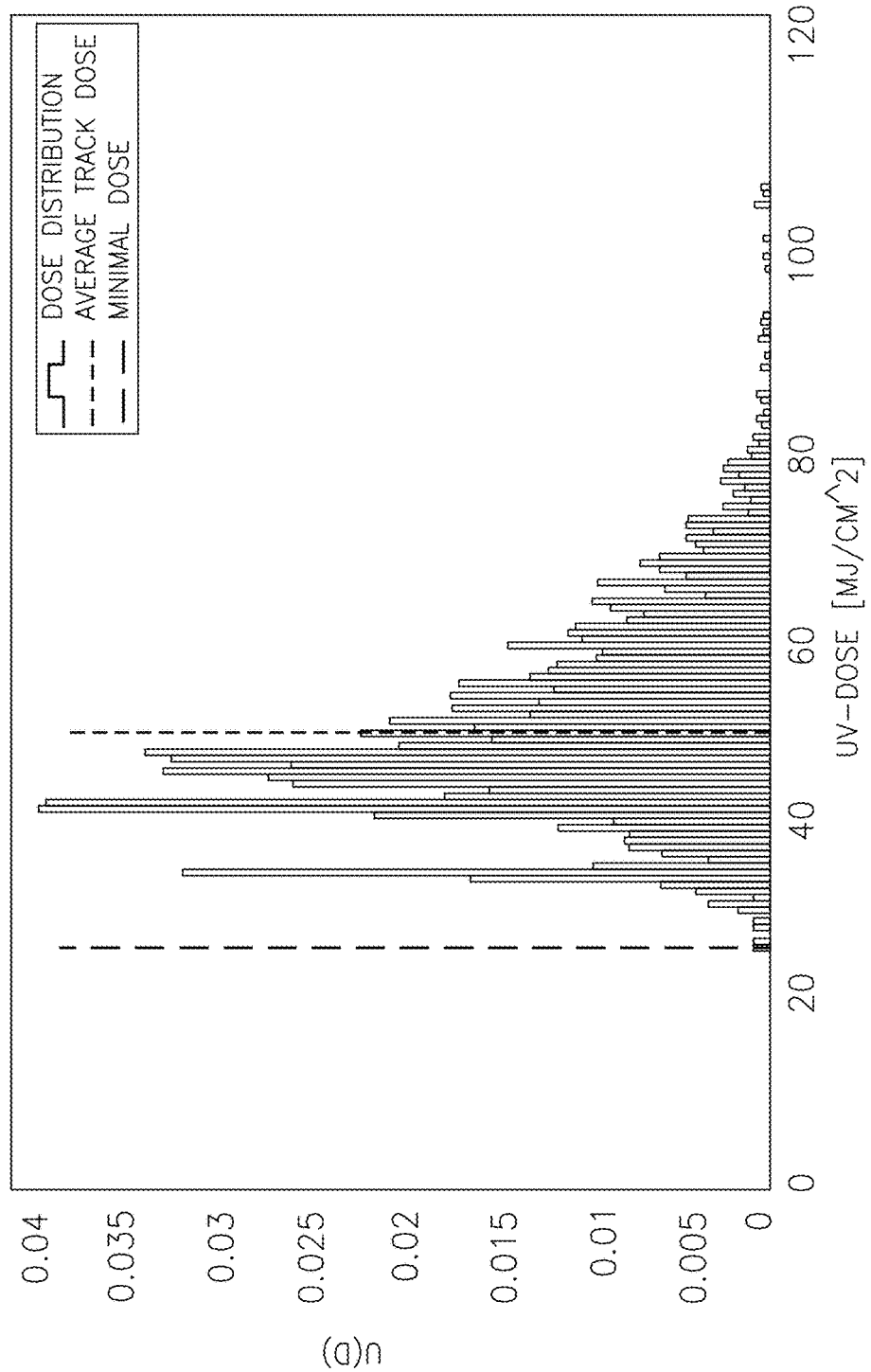
FIG. 13C is a dose distribution histogram associated with the simulation of FIGS. 13A-13B.

As comparative data, FIGS. 13A and 13B illustrate computer simulations of light flux distribution within a conventional stainless steel container having 20% reflection during a liquid disinfection process. All the other parameters used in the comparative simulation were similar to the simulations of FIGS. 12A-12C. As can be seen, the intensity of light is practically zero after 50 mm is the Z direction. FIG. 13C shows a graph illustrating the UV dose distribution within the conventional stainless steel conduit. As expected, the average dose within the stainless steel conduit having a value of {48 [mJ/cm$^2$]} is much smaller than the average dose of the quartz conduit with a value of {228 [mJ/cm$^2$]}. The dose distribution of the conventional stainless steel conduit is wider than dose distribution of the quartz conduit.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

The invention claimed is:
1. An apparatus for liquid disinfection by ultraviolet (UV) light, the apparatus comprising:
    a quartz conduit to carry flowing liquid to be disinfected; and
    a UV source positioned within the conduit substantially perpendicular to a longitudinal axis of symmetry of the conduit,
    wherein, light rays emitted from the UV source form an angle with the surface of the conduit below a critical angle for total internal reflection (TIR),
    wherein the apparatus is configured to cause at least half of the UV light rays emitted from the UV source to be totally-internally reflected at the interface of the UV light transparent conduit and its surroundings, and
    wherein the apparatus further comprises a sleeve surrounding the UV source, wherein the sleeve further comprises at least one UV-transparent object, UV-scattering object or UV reflective object which is affixed to the interior of the sleeve.
2. The apparatus of claim 1, wherein the apparatus is configured to cause at least 70% of the UV light rays emitted from the UV source to be totally-internally reflected at the interface of the UV light transparent conduit and its surroundings.
3. The apparatus of claim 1, wherein the apparatus further comprises at least one UV-transparent object, UV-scattering object or UV reflective object which is affixed to the interior of the conduit.
4. The apparatus of claim 1, further comprising one or more additional UV sources positioned within the conduit perpendicular to the longitudinal axis of the conduit.

* * * * *